United States Patent
Dillingham

(10) Patent No.: US 11,766,343 B1
(45) Date of Patent: Sep. 26, 2023

(54) ADJUSTABLE CUP FOR PROSTHESES

(71) Applicant: iFIT Prosthetics, LLC, Pewaukee, WI (US)

(72) Inventor: Timothy R. Dillingham, Philadelphia, PA (US)

(73) Assignee: iFIT Prosthetics, LLC, Pewaukee, WI (US)

( * ) Notice: Subject to any disclaimer, the term of this patent is extended or adjusted under 35 U.S.C. 154(b) by 0 days.

(21) Appl. No.: 18/095,715

(22) Filed: Jan. 11, 2023

(51) Int. Cl.
*A61F 2/80* (2006.01)
*A61F 2/76* (2006.01)
*A61F 2/50* (2006.01)

(52) U.S. Cl.
CPC ............... *A61F 2/80* (2013.01); *A61F 2/76* (2013.01); *A61F 2002/509* (2013.01); *A61F 2002/5026* (2013.01)

(58) Field of Classification Search
CPC ...... A61F 2/76; A61F 2/78; A61F 2/80; A61F 2/601; A61F 2/60; A61F 2002/509; A61F 2002/5026; A61F 2002/5083; A61F 2002/5016; A61F 2002/5021; A61F 2002/5023
See application file for complete search history.

(56) References Cited

U.S. PATENT DOCUMENTS

| | | | |
|---|---|---|---|
| 3,422,462 A | 1/1969 | Finnieston | |
| 5,405,406 A | 4/1995 | Hiemisch | |
| 6,991,657 B1 | 1/2006 | Price, Jr. | |
| 7,338,532 B2 | 3/2008 | Haberman et al. | |
| 9,050,202 B2 * | 6/2015 | Bache | A61F 2/76 |
| 9,839,536 B2 | 12/2017 | Bergande | |
| 10,363,150 B1 * | 7/2019 | Braun | A61F 2/601 |
| 2003/0233151 A1 * | 12/2003 | Lund | A61F 2/78 623/36 |
| 2005/0089363 A1 * | 4/2005 | Curtis | A61F 2/76 403/362 |
| 2005/0267600 A1 * | 12/2005 | Haberman | F16M 11/2092 403/381 |

(Continued)

FOREIGN PATENT DOCUMENTS

WO    WO-2014160865 A1 * 10/2014 ............... A61F 2/80

OTHER PUBLICATIONS

Facebook post 1 for ACA Conference of inventors with adjustable socket system. (Year: 2019).*

(Continued)

*Primary Examiner* — Christie Bahena
(74) *Attorney, Agent, or Firm* — Caesar Rivise, PC

(57) ABSTRACT

An apparatus for adjusting an expandable prosthetic device includes: an elongated main support having a longitudinal axis and a distal end, and being adapted to connect to an outer or inner side of an adjustable socket having a distal end; an adjustable cup adapted to connect to the distal end of the elongated main support and having an expandable base and at least one side adapted to move laterally toward or laterally away from the longitudinal axis of the elongated main support; and at least a portion of a suspension system disposed in the adjustable cup and having a top adapted to connect to the distal end of the adjustable socket and a bottom adapted to slidably connect to the expandable base of the adjustable cup.

30 Claims, 4 Drawing Sheets

(56) References Cited

U.S. PATENT DOCUMENTS

| | | | | |
|---|---|---|---|---|
| 2012/0101597 A1* | 4/2012 | Bache | ...................... | A61F 2/80 623/33 |
| 2014/0277584 A1* | 9/2014 | Hurley | .................... | B29C 70/42 623/33 |
| 2015/0265434 A1 | 9/2015 | Hurley et al. | | |
| 2015/0313729 A1* | 11/2015 | Williams | .................. | A61F 2/64 623/33 |
| 2016/0235560 A1 | 8/2016 | Cespedes et al. | | |
| 2019/0110910 A1* | 4/2019 | Dillingham | ............... | A61F 2/78 |
| 2020/0297514 A1* | 9/2020 | Prescott | ................ | A61F 2/7812 |
| 2020/0352748 A1* | 11/2020 | Dillingham | ............... | A61F 2/80 |

OTHER PUBLICATIONS

Facebook post 2 of video with adjustable socket of inventors (Year: 2017).*
Facebook post 3 of inventors with adjustable socket at a conference (Year: 2020).*
Ifit Transfemoral Instruction Guide. Jul. 30, 2021 (Year: 2021).*
Ifit Transfemoral instruction guide. Jun. 26, 2020 (Year: 2020).*

\* cited by examiner

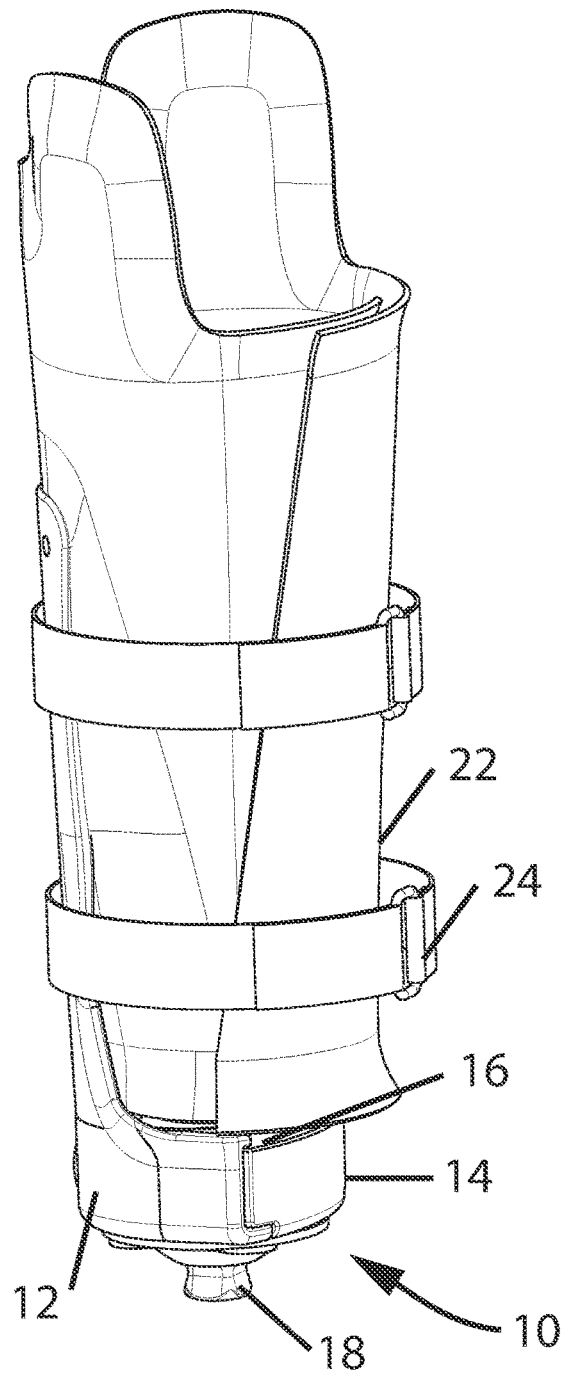
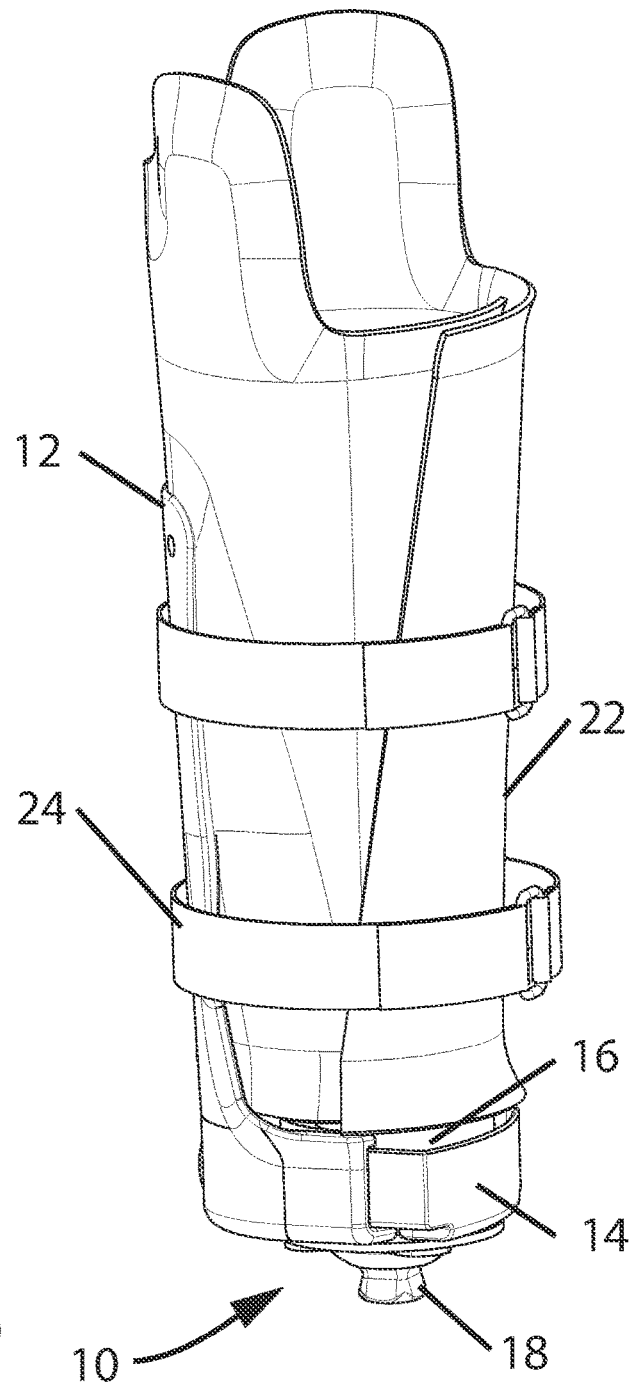
Figure 1
Figure 2

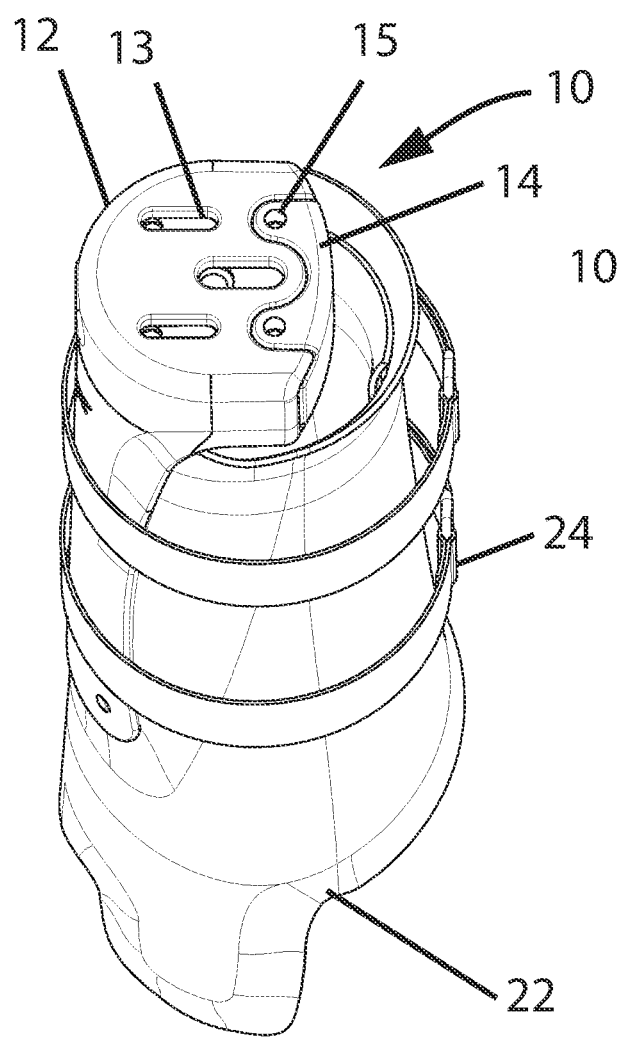
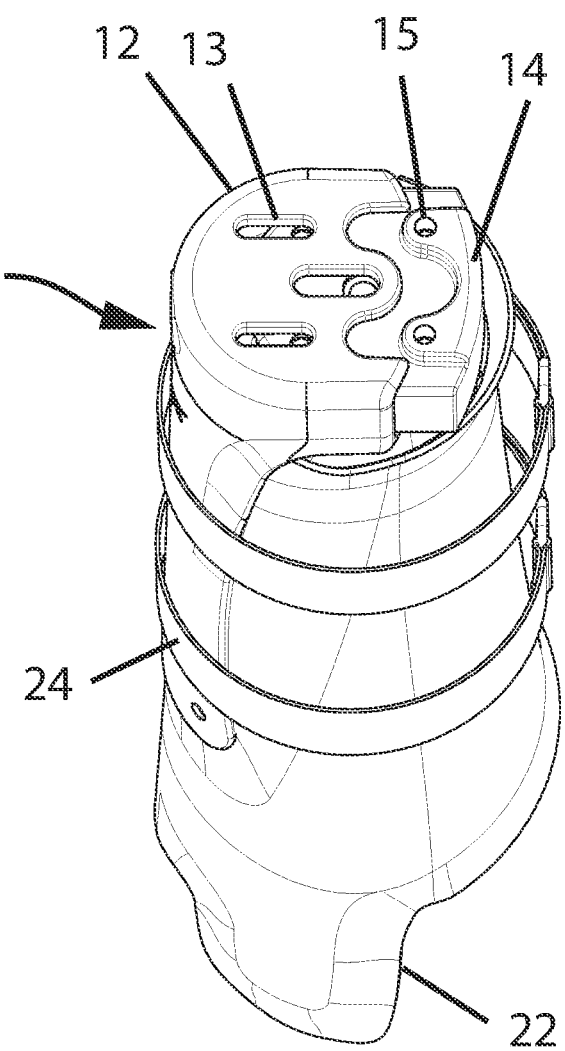
Figure 4                    Figure 5 ively made hard sockets through normal development. A comfortable, effective, and functional lower limb prosthesis during all phases of growth and development is imperative for full functional participation in age-specific activities. Conventional prostheses and prosthetic fabrication, however, are not optimally meeting the needs of this population. Skin breakdown and ulceration of the limb occurs in 74% of children and are attributable to poorly fitting prostheses. Discomfort with the prosthesis is another common complaint among children. Conventional hard sockets are expensive and do not accommodate limb growth. Because these conventional sockets rely on a one-time limb casting or 3D

ADJUSTABLE CUP FOR PROSTHESES

STATEMENT REGARDING FEDERALLY SPONSORED RESEARCH OR DEVELOPMENT

This invention(s) was made with government support under NIH Grant 1R42HD107747-01 and 4R42HD107747-02 awarded by the National Institutes of Health. The government has certain rights in the invention(s).

FIELD OF INVENTION

The present invention(s) relates to the field of prostheses, and more particularly to expandable prosthetic devices which accommodate changes in residual limb size, shape, and volume.

BRIEF DESCRIPTION OF THE DRAWINGS

Applicant's apparatus and devices will be described by way of example with reference to the accompanying drawings, in which:

FIG. 1 illustrates a perspective view of an exemplary embodiment of an expandable prosthetic device in a contracted state with an adjustable cup for adjusting the device.

FIG. 2 illustrates a perspective view of an exemplary embodiment of an expandable prosthetic device in an expanded state with an adjustable cup for adjusting the device.

FIG. 4 illustrates a perspective bottom view of an exemplary embodiment of an expandable prosthetic device with an adjustable cup for adjusting the device in a first position.

FIG. 5 illustrates a perspective bottom view of an exemplary embodiment of an expandable prosthetic device with an adjustable cup for adjusting the device in another position.

BACKGROUND

Figure 3:
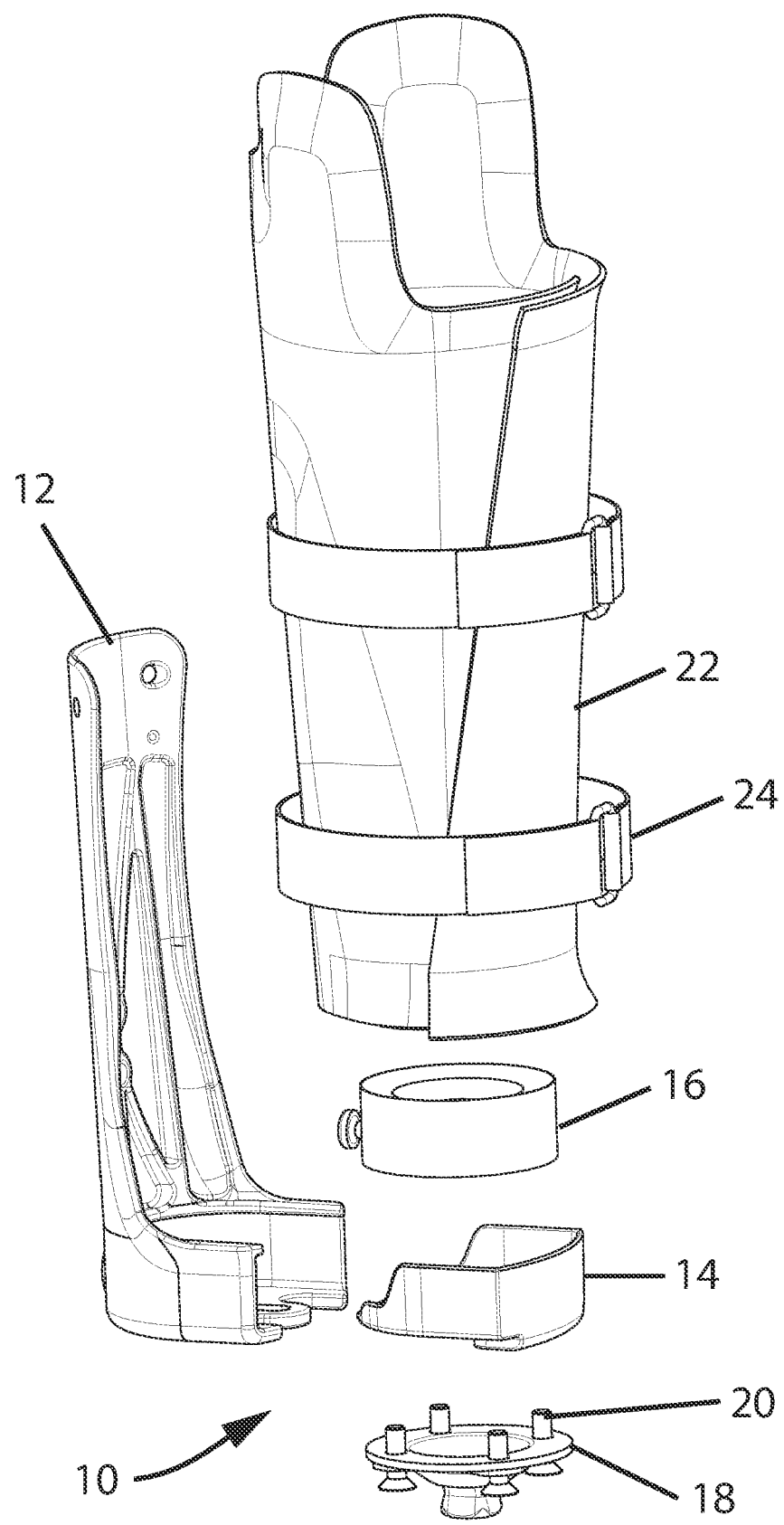
FIG. 3 illustrates an exploded view of an exemplary embodiment of an expandable prosthetic device with an adjustable cup for adjusting the device such as shown in FIGS. 1 and 2.

Children with limb loss and limb deficiencies are a group of prosthetic users who quickly grow out of their conventionally made hard sockets through normal development. A comfortable, effective, and functional lower limb prosthesis during all phases of growth and development is imperative for full functional participation in age-specific activities. Conventional prostheses and prosthetic fabrication, however, are not optimally meeting the needs of this population. Skin breakdown and ulceration of the limb occurs in 74% of children and are attributable to poorly fitting prostheses. Discomfort with the prosthesis is another common complaint among children. Conventional hard sockets are expensive and do not accommodate limb growth. Because these conventional sockets rely on a one-time limb casting or 3D limb scanning, they do not accurately account for limb soft tissue compression. Conventional socket fabrication is labor-intensive, time consuming and expensive, resulting in substantial time away from school for children and from work for parents. The need is great, therefore, for pediatric prostheses that are lower in costs, more comfortable, fit in a single visit, and which adjust and adapt to the child's growth—providing a longer time horizon for comfortable prosthesis usefulness.

Applicant's inventive solutions discussed herein also are helpful for adult patients whose limbs increase or decrease due to edema or to weight gain or loss.

It is desirable to create an adjustable prosthetic socket with a bottom that adjusts to the different circumferences of residual limbs by means of an adjustable mechanism that moves forward and backward.

It is desirable to create such an adjustable mechanism that can be fixed at different distances from a starting position to accommodate different sized residual limbs.

It is desirable to create such an adjustable mechanism that can be connected to a plurality of types of adjustable upper sockets to adjustably grasp the residual limb.

It is desirable to create an adjustable mechanism that can accommodate growing limbs particularly of children and adolescents.

It is desirable to create an adjustable mechanism that can accommodate adult patients whose limbs increase or decrease due to edema or to weight gain or loss.

It is desirable to create an adjustable cup with a radial movement that serves to adjust and accommodate limbs of different circumferences.

It is desirable to create an adjustable mechanism for such an adjustable cup that can be fixed at different distances from a starting position to accommodate different sized residual limbs.

It is desirable to create such an adjustable mechanism that can be connected to a plurality of types of adjustable upper sockets to adjustably grasp the residual limb.

Persons skilled in the art will recognize that Applicant's apparatus, devices, systems, and methods disclosed herein and illustrated in the drawings address and solve those and other problems not previously addressed by the prior art, and also overcome many deficiencies of the prior art due to the various benefits and advantages of Applicant's apparatus, devices, systems, and methods, which advantages and benefits will become apparent to such persons upon review of the drawings and the complete disclosure herein.

BRIEF SUMMARY

There are various aspects of Applicant's apparatus, systems, devices, and methods, and many variations of each aspect.

One such aspect is an apparatus for adjusting an expandable prosthetic device, including: an elongated main support having a longitudinal axis and a distal end, and being adapted to connect to an outer or inner side of an adjustable socket having a distal end; an adjustable cup adapted to connect to the distal end of the elongated main support and having an expandable base and at least one side adapted to move laterally toward or laterally away from the longitudinal axis of the elongated main support; and at least a portion of a suspension system disposed in the adjustable cup and having a top adapted to connect to the distal end of the adjustable socket and a bottom adapted to slidably connect to the expandable base of the adjustable cup. As noted above, there are many variations of this aspect.

In a first variation of the apparatus the expandable base includes first and second overlapping planar pieces slidably connected and having at least one aperture in each of said overlapping planar pieces, and at least one aperture in the first overlapping planar piece aligns with at least one aperture in the second overlapping planar piece when said first and second overlapping planar pieces are slidably moved from a first position to a second position. There are a variety of variants of this variation.

In one variant of the first variation of the apparatus, at least one of the apertures has a shape selected from a group comprising circular, slot-like, non-circular, or a combination thereof.

In another variant of the first variation of the apparatus, a securing piece is inserted in at least one of the apertures.

In a second variation of the apparatus the elongated main support includes a first upright portion and a second upright portion overlapping at least a portion of the first upright portion, at least one of said first and second upright portions being adapted to flex laterally toward or laterally away from the longitudinal axis of the elongated main support; and a first side of the adjustable cup is expandable and connected to the first upright portion and a second side of the adjustable cup is expandable and connected to the second upright portion, and at least a portion of the first side of the adjustable cup is overlapped by at least a portion of the second side of the adjustable cup. There are a variety of variants of this variation.

In one variant of the second variation of the apparatus the at least a portion of the suspension system has at least one aperture in the bottom; and at least one aperture in the expandable base of the adjustable cup aligns with the at least one aperture in the bottom of the at least a portion of the suspension system when at least one of said first and second sides of the adjustable cup is expanded or retracted. There are various variants of this variant.

In one such variant, at least one of the apertures has a shape selected from a group comprising circular, slot-like, non-circular, or a combination thereof.

In another such variant, a securing piece is inserted in at least one of the apertures.

In a third variation of the apparatus the suspension system is selected from a group comprising a pin suspension system having a shuttle lock or puck, a magnetic suspension system, a Velcro suspension system, a suction suspension system, a lanyard suspension system, a clasp suspension system, a hooks suspension system, or combinations thereof.

Another aspect is a first expandable prosthetic device, including: an elongated adjustable socket having an outer side, an inner side, and a distal end; an elongated main support having a longitudinal axis and a distal end, and being adapted to connect to the outer side or the inner side of the elongated adjustable socket; an adjustable cup adapted to connect to the distal end of the elongated main support and having an expandable base and at least one side adapted to move laterally toward or laterally away from the longitudinal axis of the elongated main support; and at least a portion of a suspension system disposed in the adjustable cup and having a top adapted to connect to the distal end of the adjustable socket and a bottom adapted to slidably connect to the expandable base of the adjustable cup. As noted above, there are many variations of this aspect.

In a first variation of the first expandable prosthetic device, the expandable base includes first and second overlapping planar pieces slidably connected and having at least one aperture in each of said overlapping planar pieces, and at least one aperture in the first overlapping planar piece aligns with at least one aperture in the second overlapping planar piece when said first and second overlapping planar pieces are slidably moved from a first position to a second position. There are a variety of variants of this variation.

In one variant of the first variation of the first expandable prosthetic device, at least one of the apertures has a shape selected from a group comprising circular, slot-like, non-circular, or a combination thereof.

In another variant of the first variation of the first expandable prosthetic device, a securing piece is inserted in at least one of the apertures.

In a second variation of the first expandable prosthetic device, the elongated main support includes a first upright portion and a second upright portion overlapping at least a portion of the first upright portion, at least one of said first and second upright portions being adapted to flex laterally toward or laterally away from the longitudinal axis of the elongated main support; and a first side of the adjustable cup is expandable and connected to the first upright portion and a second side of the adjustable cup is expandable and connected to the second upright portion, and at least a portion of the first side of the adjustable cup is overlapped by at least a portion of the second side of the adjustable cup. There are a variety of variants of this variation.

In one variant of the second variation of the first expandable prosthetic device, the at least a portion of the suspension system has at least one aperture in the bottom; and at least one aperture in the expandable base of the adjustable cup aligns with the at least one aperture in the bottom of the at least a portion of the suspension system when at least one of said first and second sides of the adjustable cup is expanded or retracted. There are various variants of this variant.

In one such variant, at least one of the apertures has a shape selected from a group comprising circular, slot-like, non-circular, or a combination thereof.

In another such variant, a securing piece is inserted in at least one of the apertures.

In a third variation of the first expandable prosthetic device, the suspension system is selected from a group comprising a pin suspension system having a shuttle lock or puck, a magnetic suspension system, a Velcro suspension system, a suction suspension system, a lanyard suspension system, a clasp suspension system, a hooks suspension system, or combinations thereof.

A second expandable prosthetic device is similar to the first expandable prosthetic device but also includes at least one closure mechanism adapted to adjust the elongated adjustable socket selected from a group comprising straps, looped cables, laces, buckles, cable protuberances, buttons, snaps, clasps, clips, elastic components, ties, interlocking components, hook-and-loop fasteners, hook-and-eye fasteners, hook-shaped components, or combinations thereof. There are many variations and variants of the second expandable prosthetic device similar to the many variations and variants described above for the first expandable prosthetic device.

A third expandable prosthetic device is similar to the first expandable prosthetic device but also includes an adapter adapted to connect to the expandable base of the adjustable cup selected from a group comprising a pyramid adapter, a pyramid receiver, an offset pyramid, a rotating pyramid, or combinations thereof. There are many variations and variants of the third expandable prosthetic device similar to the many variations and variants described above for the first expandable prosthetic device.

Another aspect is a method for adjusting an expandable prosthetic device, including multiple steps. The first step is providing an elongated main support having a longitudinal axis and a distal end, and being adapted to connect to an outer or inner side of an adjustable socket having a distal end. The second step is providing an adjustable cup adapted to connect to the distal end of the elongated main support and having an expandable base and at least one side adapted to move laterally toward or laterally away from the longitudinal axis of the elongated main support. The third step is providing at least a portion of a suspension system disposed in the adjustable cup and having a top adapted to connect to the distal end of the adjustable socket and a bottom adapted to slidably connect to the expandable base of the adjustable cup. The fourth step is moving the at least one side of the expandable base of the adjustable cup laterally toward or laterally away from the longitudinal axis of the elongated main support.

In a first variation of a method for adjusting an expandable prosthetic device, the expandable base includes first and second overlapping planar pieces slidably connected and having at least one aperture in each of said overlapping planar pieces, and at least one aperture in the first overlapping planar piece aligns with at least one aperture in the second overlapping planar piece when said first and second overlapping planar pieces are slidably moved from a first position to a second position. There are a variety of variants of this variation.

In one variant of the first variation of the method for adjusting an expandable prosthetic device, at least one of the apertures has a shape selected from a group comprising circular, slot-like, non-circular, or a combination thereof.

In another variant of the first variation of the method for adjusting an expandable prosthetic device, a securing piece is inserted in at least one of the apertures.

In a second variation of a method for adjusting an expandable prosthetic device, the elongated main support includes a first upright portion and a second upright portion overlapping at least a portion of the first upright portion, at least one of said first and second upright portions being adapted to flex laterally toward or laterally away from the longitudinal axis of the elongated main support; and a first side of the adjustable cup is expandable and connected to the first upright portion and a second side of the adjustable cup is expandable and connected to the second upright portion, and at least a portion of the first side of the adjustable cup is overlapped by at least a portion of the second side of the adjustable cup. There are a variety of variants of this variation.

In one variant of the second variation of a method for adjusting an expandable prosthetic device, the at least a portion of the suspension system has at least one aperture in the bottom; and at least one aperture in the expandable base of the adjustable cup aligns with the at least one aperture in the bottom of the at least a portion of the suspension system when at least one of said first and second sides of the adjustable cup is expanded or retracted. There are various variants of this variant.

In one such variant, at least one of the apertures has a shape selected from a group comprising circular, slot-like, non-circular, or a combination thereof.

In another such variant, a securing piece is inserted in at least one of the apertures.

In a third variation of a method for adjusting an expandable prosthetic device, the suspension system is selected from a group comprising a pin suspension system having a shuttle lock or puck, a magnetic suspension system, a Velcro suspension system, a suction suspension system, a lanyard suspension system, a clasp suspension system, a hooks suspension system, or combinations thereof.

Another aspect is a first method for expanding a prosthetic device. The method includes multiple steps. The first step is providing an elongated adjustable socket having an outer side, an inner side, and a distal end. The second step is providing an elongated main support having a longitudinal axis and a distal end, and being adapted to connect to the outer side or the inner side of the elongated adjustable socket. The third step is providing an adjustable cup adapted to connect to the distal end of the elongated main support and having an expandable base and at least one side adapted to move laterally toward or laterally away from the longitudinal axis of the elongated main support. The fourth step is providing at least a portion of a suspension system disposed in the adjustable cup and having a top adapted to connect to the distal end of the adjustable socket and a bottom adapted to slidably connect to the expandable base of the adjustable cup. The fifth step is moving the at least one side of the expandable base of the adjustable cup laterally toward or laterally away from the longitudinal axis of the elongated main support.

In a first variation of a first method for expanding a prosthetic device, the expandable base includes first and second overlapping planar pieces slidably connected and having at least one aperture in each of said overlapping planar pieces, and at least one aperture in the first overlapping planar piece aligns with at least one aperture in the second overlapping planar piece when said first and second overlapping planar pieces are slidably moved from a first position to a second position. There are a variety of variants of this variation.

In one variant of the first variation of the first method for expanding a prosthetic device, at least one of the apertures has a shape selected from a group comprising circular, slot-like, non-circular, or a combination thereof.

In another variant of the first variation of the first method for expanding a prosthetic device, a securing piece is inserted in at least one of the apertures.

In a second variation of a first method for expanding a prosthetic device, the elongated main support includes a first upright portion and a second upright portion overlapping at least a portion of the first upright portion, at least one of said first and second upright portions being adapted to flex laterally toward or laterally away from the longitudinal axis of the elongated main support; and a first side of the adjustable cup is expandable and connected to the first upright portion and a second side of the adjustable cup is expandable and connected to the second upright portion, and at least a portion of the first side of the adjustable cup is overlapped by at least a portion of the second side of the adjustable cup. There are a variety of variants of this variation.

In one variant of the second variation of a first method for expanding a prosthetic device, the at least a portion of the suspension system has at least one aperture in the bottom; and at least one aperture in the expandable base of the adjustable cup aligns with the at least one aperture in the bottom of the at least a portion of the suspension system when at least one of said first and second sides of the adjustable cup is expanded or retracted. There are a variety of variants of this variation.

In one such variant, at least one of the apertures has a shape selected from a group comprising circular, slot-like, non-circular, or a combination thereof.

In another such variant, a securing piece is inserted in at least one of the apertures.

In a third variation of a first method for expanding a prosthetic device, the suspension system is selected from a group comprising a pin suspension system having a shuttle lock or puck, a magnetic suspension system, a Velcro suspension system, a suction suspension system, a lanyard suspension system, a clasp suspension system, a hooks suspension system, or combinations thereof.

A second method for expanding a prosthetic device is similar to the first method for expanding a prosthetic device but includes two additional steps. The first additional step is providing at least one closure mechanism adapted to adjust the elongated adjustable socket selected from a group comprising straps, looped cables, laces, buckles, cable protuberances, buttons, snaps, clasps, clips, elastic components, ties, interlocking components, hook-and-loop fasteners, hook-and-eye fasteners, hook-shaped components, or combinations thereof. The second additional step is to adjust the elongated adjustable socket with the closure mechanism. There are many variations and variants of the second method for expanding a prosthetic device similar to the many variations and variants described above for the first method for expanding a prosthetic device.

A third method for expanding a prosthetic device is similar to the first method for expanding a prosthetic device but includes two additional steps. The first additional step is to provide an adapter adapted to connect to the expandable base of the adjustable cup selected from a group comprising a pyramid adapter, a pyramid receiver, an offset pyramid, a rotating pyramid, or combinations thereof. The second additional step is to connect the adapter to the expandable base of the adjustable cup. There are many variations and variants of the third method for expanding a prosthetic device similar to the many variations and variants described above for the first method for expanding a prosthetic device.

DETAILED DESCRIPTION

For the purpose of promoting an understanding of the present invention(s), references are made herein to several exemplary embodiments of Applicant's adjustable cup and expandable prosthetic device with an adjustable cup, only some of which are described herein. It should be understood that no limitations on the scope of the invention(s) are intended by describing these exemplary embodiments.

One of ordinary skill in the art will readily appreciate that alternate but functionally equivalent materials, components, and designs may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ Applicant's apparatus, devices, systems, and methods.

It should be understood that the drawings are not necessarily to scale; instead, emphasis has been placed upon illustrating the principles of the invention(s). In addition, in the embodiments depicted herein, like reference numerals in the various drawings refer to identical or near identical structural elements.

Applicant's apparatus, devices, systems, and methods are widely applicable to many embodiments, as is readily apparent from the disclosure herein. Those skilled in the art will recognize that Applicant's apparatus, devices, systems, and methods may be practiced with modification and alteration without departing from the teachings disclosed herein.

Applicant's adjustable cup allows the center of a prosthetic pin suspension system (with a puck or shuttle lock) to be moved rearward and accommodate larger limbs with the adjustable cup. The sliding mechanism of the adjustable cup adjusts easily to accommodate limb growth as in the case of children who are growing or adults whose limb increases due to edema or to weight gain. The adjustable cup allows a socket to easily accommodate different limb sizes and it works with various types of sockets and closure mechanisms.

In the exemplary embodiments shown in FIGS. 1 and 2 the adjustable cup 10 at the bottom of the main support 12 moves forward and rearward to increase the circumference of the adjustable socket 22. As shown in FIG. 3, a pin suspension shuttle lock 16 sits in the sliding piece 14 of the adjustable cup 10 and moves with the sliding piece. There are any number of suspension systems in the art that could fit within this slidable piece and which suspend the socket on the limb-magnetic, Velcro, suction, lanyard, etc. The upright portion or main support 12 of the adjustable cup 10 is attached to the adjustable socket 22 via screws 20, bolts, or other fasteners or mechanisms of attachment. The adjustable socket 22 wraps around the residual limb and encloses the residual limb by means of closure mechanisms 24, as shown in FIGS. 1-3. These closure mechanisms may be any of a variety of buckles, clasps, straps, or other closure means.

FIG. 1 shows an expandable prosthetic device in a contracted state. The main support 12 allows for the sliding piece 14 to slide along an axis moving the shuttle lock 16 and the pyramid adapter 18 further from the main support 12. The adjustable socket 22 is secured to the main support 12. The adjustable socket 22 secures to the residual limb with one or more closure mechanisms 24. FIG. 2 shows the expandable prosthetic device in an expanded state. A benefit of the sliding piece 14 is that the shuttle lock 16 and the pyramid adapter 18 are moved away from the main support 12 to fit a larger residual limb. The adjustable socket 22 accommodates the larger circumference to accommodate the residual limb when the sliding piece 14 moves rearward.

FIG. 3 shows an embodiment of the expandable prosthetic device in an exploded view. The shuttle lock 16 is attached to the adjustable cup 10 by screws 20 that pass through the pyramid adapter 18 and through the bottom surface of the main support 12 and the bottom surface of the sliding piece 14. The screws secure those components of the expandable prosthetic device once put into the proper placement and prevent the components from moving. Persons skilled in the art will recognize that the pyramid adapter 18 shown in this exemplary embodiment can be replaced with any number of connector plates and mechanisms that are common in the industry such as for example a pyramid receiver, offset pyramid, or rotating pyramid.

FIG. 4 shows the slots 13 in the main support 12 and the holes 15 in the sliding piece 14 that allow for the shuttle lock 16 and the pyramid adapter 18 to be connected and secured by the screws 20.

In FIG. 5 the sliding piece 14 is extended rearward and in this position accommodates a larger residual limb. In FIG. 4, sliding piece 14 is in its closed position and this configuration is used for someone with a smaller residual limb.

Figure 6:
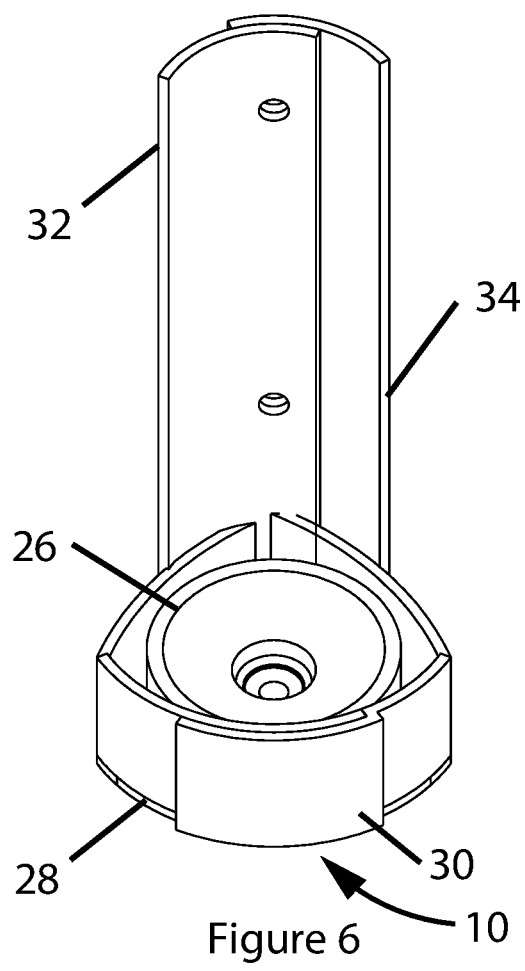
FIG. 6 illustrates a perspective view of another exemplary embodiment of an adjustable cup for adjusting an expandable prosthetic device in a first position.
Figure 7:
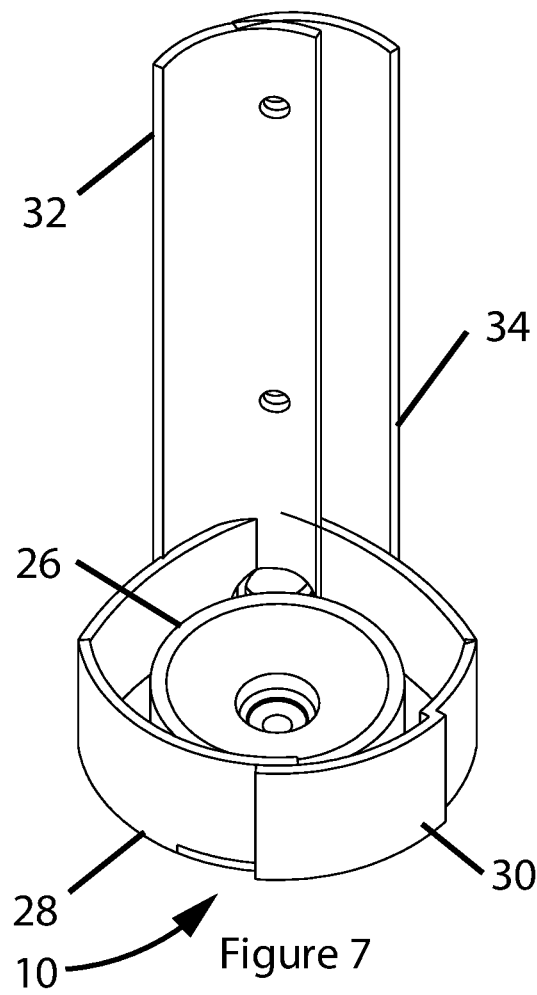
FIG. 7 illustrates a perspective view of another exemplary embodiment of an adjustable cup for adjusting an expandable prosthetic device in another position.

FIGS. 6-9 show other exemplary embodiments of the adjustable cup 10 for use in an expandable prosthetic device. In this adjustable cup 10 the sides of the inner expandable part 28 and the outer expandable part 30 move outward in a lateral direction when the puck (shuttle lock) 26 is moved rearward. The puck 26 is mounted with the screws 20 (such as in FIG. 3) in the position desired. The first upright portion 32 and the second upright portion 34 move to accommodate an outward shift (or an inward shift) of the inner expandable part 28 and the outer expandable part 30, as best seen in FIGS. 6 and 7.

The expandable prosthetic device of the embodiment in the contracted state creates a wider base at the same time moving the puck 26 and the pyramid adapter (not shown) back. The main support in this embodiment includes the first upright portion 32 and the second upright portion 34 that pivot or flex along the front and the inner expandable part 28 and the outer expandable part 30, which two parts each slide with respect to each other. The slots 36 in the bottom of the puck (shuttle lock) 26 provide for directional guidance for the movement of the puck rearward, and the lateral outward movement of the two sides of the inner expandable part 28 and the outer expandable part 30.

Figure 8:
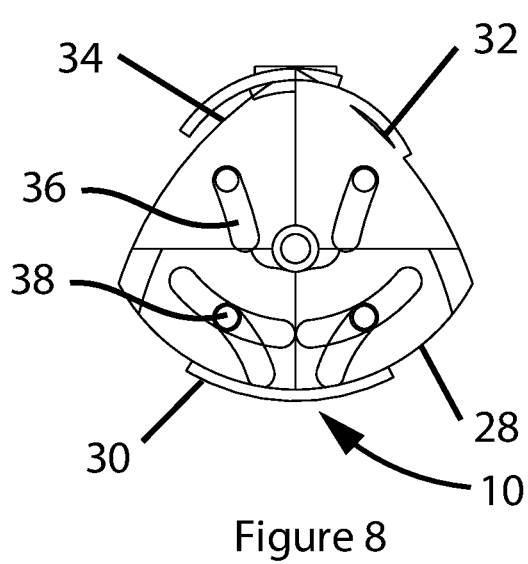
FIG. 8 illustrates a perspective bottom view of the adjustable cup shown in FIG. 6.
Figure 9:
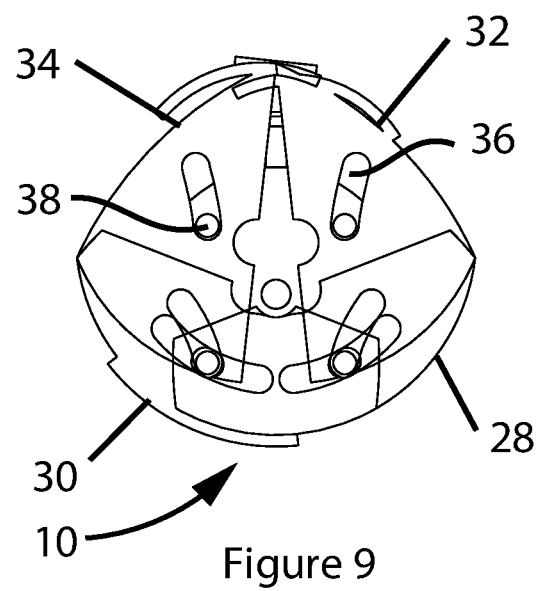
FIG. 9 illustrates a perspective bottom view of the adjustable cup shown in FIG. 7.

FIG. 8 shows the arrangement of slots 36 and holes 38 to allow the puck (shuttle lock) 26 to slide back from the main support. FIGS. 6 and 8 show the puck 26 in the forward most position (smallest diameter to accommodate the residual limb). In FIGS. 7 and 9 the puck 26 is moved to its maximum rearward position resulting in the maximal expansion of the inner expandable part 28 and the outer expandable part 30 away from each other. This mechanism adjusts to residual limb differences and expands laterally to provide a larger base of support for the person's limb in the socket.

Applicant's adjustable cup provides highly useful adjustability that is an integral part of adjustable socket technology. It adjusts in a manner to expand the circumference of the prosthetic socket to accommodate childhood growth by means of a rearward or forward sliding motion. This adjustability is an important advancement as it maintains a low profile cup for the socket, yet provides considerable expandability. It will allow multiple adjustments over the course of time to allow and accommodate growth in a child or an adolescent, as well as some adults, without the need for a complete socket revision. This is a cost effective means of providing long term comfort to growing children and teenagers.

In the exemplary embodiments shown in the drawings and discussed in the Detailed Description, various fasteners and adjustment components are used, including screws and closure mechanisms. Persons skilled in the art will recognize that other types of fasteners (bolts, etc.) and other types of closure mechanisms could be used as well instead of those shown and discussed. For example, various types of components may be used for closing, tightening, and securing, including straps, looped cables, laces, buckles, cable protuberances, buttons, snaps, clasps, clips, elastic components, ties, interlocking components, hook-and-loop fasteners, hook-and-eye fasteners, hook-shaped components, and any combination of these and other structures and devices.

Applicant's apparatus and devices include many other embodiments and variations thereof which are not illustrated in the drawings or discussed in the Detailed Description section. Those embodiments and variations, however, do fall within the scope of the appended claims and equivalents thereof.

Persons skilled in the art will recognize that the embodiments and variations illustrated in the drawings and discussed in the Detailed Description section do not disclose all of the possible arrangements of Applicant's apparatus and devices, and that other arrangements are possible. Accordingly, all such other arrangements are contemplated by Applicant's apparatus and devices, and are within the scope of the appended claims and equivalents thereof.

Persons skilled in the art also will recognize that many other embodiments incorporating Applicant's inventive concepts are possible, as well as many variations of the embodiments illustrated and described herein.

Although illustrated and described herein with reference to certain specific embodiments, Applicant's apparatus and devices are nevertheless not intended to be limited to the details shown. Rather, various modifications may be made in the details within the scope and range of equivalents of the claims without departing from the spirit of the invention.

What is claimed is:

1. An apparatus for adjusting an expandable prosthetic device, comprising:
    an elongated main support having a longitudinal axis and a distal end, and being adapted to connect to an outer or inner side of an adjustable socket having a distal end;
    an adjustable cup adapted to connect to the distal end of the elongated main support and having an expandable base and at least one side adapted to move laterally toward or laterally away from the longitudinal axis of the elongated main support; and
    at least a portion of a suspension system disposed in the adjustable cup and having a top adapted to connect to the distal end of the adjustable socket and a bottom adapted to slidably connect to the expandable base of the adjustable cup.

2. An apparatus as in claim 1,
    wherein the expandable base includes first and second overlapping planar pieces slidably connected and having at least one aperture in each of said overlapping planar pieces, and
    wherein at least one aperture in the first overlapping planar piece aligns with at least one aperture in the second overlapping planar piece when said first and second overlapping planar pieces are slidably moved from a first position to a second position.

3. An apparatus as in claim 2, wherein at least one of the apertures has a shape selected from a group comprising circular, slot-like, non-circular, or a combination thereof.

4. An apparatus as in claim 2, wherein a securing piece is inserted in at least one of the apertures.

5. An apparatus as in claim 1,
    wherein the elongated main support includes a first upright portion and a second upright portion overlapping at least a portion of the first upright portion, at least one of said first and second upright portions being adapted to flex laterally toward or laterally away from the longitudinal axis of the elongated main support; and
    wherein a first side of the adjustable cup is expandable and connected to the first upright portion and a second side of the adjustable cup is expandable and connected to the second upright portion, and at least a portion of the first side of the adjustable cup is overlapped by at least a portion of the second side of the adjustable cup.

6. An apparatus as in claim 5,
    wherein the at least a portion of the suspension system has at least one aperture in the bottom; and
    wherein at least one aperture in the expandable base of the adjustable cup aligns with the at least one aperture in the bottom of the at least a portion of the suspension system when at least one of said first and second sides of the adjustable cup is expanded or retracted.

7. An apparatus as in claim 6, wherein at least one of the apertures has a shape selected from a group comprising circular, slot-like, non-circular, or a combination thereof.

8. An apparatus as in claim 6, wherein a securing piece is inserted in at least one of the apertures.

9. An apparatus as in claim 1, wherein the suspension system is selected from a group comprising a pin suspension system having a shuttle lock or puck, a magnetic suspension system, a suction suspension system, a lanyard suspension system, or combinations thereof.

10. An expandable prosthetic device, comprising:
an elongated adjustable socket having an outer side, an inner side, and a distal end;
an elongated main support having a longitudinal axis and a distal end, and being adapted to connect to the outer side or the inner side of the elongated adjustable socket;
an adjustable cup adapted to connect to the distal end of the elongated main support and having an expandable base and at least one side adapted to move laterally toward or laterally away from the longitudinal axis of the elongated main support; and
at least a portion of a suspension system disposed in the adjustable cup and having a top adapted to connect to the distal end of the adjustable socket and a bottom adapted to slidably connect to the expandable base of the adjustable cup.

11. An expandable prosthetic device as in claim 10,
wherein the expandable base includes first and second overlapping planar pieces slidably connected and having at least one aperture in each of said overlapping planar pieces, and
wherein at least one aperture in the first overlapping planar piece aligns with at least one aperture in the second overlapping planar piece when said first and second overlapping planar pieces are slidably moved from a first position to a second position.

12. An expandable prosthetic device as in claim 11, wherein at least one of the apertures has a shape selected from a group comprising circular, slot-like, non-circular, or a combination thereof.

13. An expandable prosthetic device as in claim 11, wherein a securing piece is inserted in at least one of the apertures.

14. An expandable prosthetic device as in claim 10,
wherein the elongated main support includes a first upright portion and a second upright portion overlapping at least a portion of the first upright portion, at least one of said first and second upright portions being adapted to flex laterally toward or laterally away from the longitudinal axis of the elongated main support; and
wherein a first side of the adjustable cup is expandable and connected to the first upright portion and a second side of the adjustable cup is expandable and connected to the second upright portion, and at least a portion of the first side of the adjustable cup is overlapped by at least a portion of the second side of the adjustable cup.

15. An expandable prosthetic device as in claim 14,
wherein the at least a portion of the suspension system has at least one aperture in the bottom; and
wherein at least one aperture in the expandable base of the adjustable cup aligns with the at least one aperture in the bottom of the at least a portion of the suspension system when at least one of said first and second sides of the adjustable cup is expanded or retracted.

16. An expandable prosthetic device as in claim 15, wherein at least one of the apertures has a shape selected from a group comprising circular, slot-like, non-circular, or a combination thereof.

17. An expandable prosthetic device as in claim 15, wherein a securing piece is inserted in at least one of the apertures.

18. An expandable prosthetic device as in claim 10, wherein the suspension system is selected from a group comprising a pin suspension system having a shuttle lock or puck, a magnetic suspension system, a suction suspension system, a lanyard suspension system, or combinations thereof.

19. An expandable prosthetic device as in claim 10, further comprising at least one closure mechanism adapted to adjust the elongated adjustable socket selected from a group comprising straps, looped cables, laces, buckles, cable protuberances, buttons, snaps, clasps, clips, elastic components, ties, interlocking components, hook-and-loop fasteners, hook-and-eye fasteners, hook-shaped components, or combinations thereof.

20. An expandable prosthetic device as in claim 10, further comprising an adapter adapted to connect to the expandable base of the adjustable cup selected from a group comprising a pyramid adapter, a pyramid receiver, an offset pyramid, a rotating pyramid, or combinations thereof.

21. A method for adjusting an expandable prosthetic device, comprising:
providing an elongated main support having a longitudinal axis and a distal end, and being adapted to connect to an outer or inner side of an adjustable socket having a distal end;
providing an adjustable cup adapted to connect to the distal end of the elongated main support and having an expandable base and at least one side adapted to move laterally toward or laterally away from the longitudinal axis of the elongated main support;
providing at least a portion of a suspension system disposed in the adjustable cup and having a top adapted to connect to the distal end of the adjustable socket and a bottom adapted to slidably connect to the expandable base of the adjustable cup;
moving the at least one side of the expandable base of the adjustable cup laterally toward or laterally away from the longitudinal axis of the elongated main support.

22. A method as in claim 21,
wherein the expandable base includes first and second overlapping planar pieces slidably connected and having at least one aperture in each of said overlapping planar pieces, and
wherein at least one aperture in the first overlapping planar piece aligns with at least one aperture in the second overlapping planar piece when said first and second overlapping planar pieces are slidably moved from a first position to a second position.

23. A method as in claim 21,
wherein the elongated main support includes a first upright portion and a second upright portion overlapping at least a portion of the first upright portion, at least one of said first and second upright portions being adapted to flex laterally toward or laterally away from the longitudinal axis of the elongated main support; and
wherein a first side of the adjustable cup is expandable and connected to the first upright portion and a second side of the adjustable cup is expandable and connected to the second upright portion, and at least a portion of the first side of the adjustable cup is overlapped by at least a portion of the second side of the adjustable cup.

24. A method as in claim 23,
wherein the at least a portion of the suspension system has at least one aperture in the bottom; and
wherein at least one aperture in the expandable base of the adjustable cup aligns with the at least one aperture in the bottom of the at least a portion of the suspension system when at least one of said first and second sides of the adjustable cup is expanded or retracted.

25. A method as in claim 21, wherein the suspension system is selected from a group comprising a pin suspension system having a shuttle lock or puck, a magnetic suspension system, a suction suspension system, a lanyard suspension system, or combinations thereof.

26. A method for expanding a prosthetic device, comprising:
   providing an elongated adjustable socket having an outer side, an inner side, and a distal end;
   providing an elongated main support having a longitudinal axis and a distal end, and being adapted to connect to the outer side or the inner side of the elongated adjustable socket;
   providing an adjustable cup adapted to connect to the distal end of the elongated main support and having an expandable base and at least one side adapted to move laterally toward or laterally away from the longitudinal axis of the elongated main support;
   providing at least a portion of a suspension system disposed in the adjustable cup and having a top adapted to connect to the distal end of the adjustable socket and a bottom adapted to slidably connect to the expandable base of the adjustable cup; and
   moving the at least one side of the expandable base of the adjustable cup laterally toward or laterally away from the longitudinal axis of the elongated main support.

27. A method for expanding a prosthetic device as in claim 26,
   wherein the expandable base includes first and second overlapping planar pieces slidably connected and having at least one aperture in each of said overlapping planar pieces, and
   wherein at least one aperture in the first overlapping planar piece aligns with at least one aperture in the second overlapping planar piece when said first and second overlapping planar pieces are slidably moved from a first position to a second position.

28. A method for expanding a prosthetic device as in claim 26,
   wherein the elongated main support includes a first upright portion and a second upright portion overlapping at least a portion of the first upright portion, at least one of said first and second upright portions being adapted to flex laterally toward or laterally away from the longitudinal axis of the elongated main support; and
   wherein a first side of the adjustable cup is expandable and connected to the first upright portion and a second side of the adjustable cup is expandable and connected to the second upright portion, and at least a portion of the first side of the adjustable cup is overlapped by at least a portion of the second side of the adjustable cup.

29. A method for expanding a prosthetic device as in claim 28,
   wherein the at least a portion of the suspension system has at least one aperture in the bottom; and
   wherein at least one aperture in the expandable base of the adjustable cup aligns with the at least one aperture in the bottom of the at least a portion of the suspension system when at least one of said first and second sides of the adjustable cup is expanded or retracted.

30. A method for expanding a prosthetic device as in claim 26, wherein the suspension system is selected from a group comprising a pin suspension system having a shuttle lock or puck, a magnetic suspension system, a suction suspension system, a lanyard suspension system, or combinations thereof.

* * * * *